United States Patent [19]

Helting

[11] 4,033,819

[45] July 5, 1977

[54] DERIVATIVES OF DIPHTHERIA TOXIN, PROCESS FOR PREPARING THEM AND AGENTS CONTAINING THEM

[75] Inventor: Torsten Bertil Helting, Marbach-Marburg an der Lahn, Germany

[73] Assignee: Behringwerke Aktiengesellschaft, Marburg an der Lahn, Germany

[22] Filed: Oct. 9, 1975

[21] Appl. No.: 621,238

[30] Foreign Application Priority Data

Oct. 11, 1974 Germany .......................... 2448530

[52] U.S. Cl. .................................. 195/29; 424/92
[51] Int. Cl.² ...................... C12D 7/00; C12K 5/00
[58] Field of Search ........................................ 195/29

[56] References Cited

UNITED STATES PATENTS 3,888,837  6/1975  Tsumita et al. ...................... 195/29

*Primary Examiner*—Lionel M. Shapiro
*Assistant Examiner*—Robert J. Warden
*Attorney, Agent, or Firm*—Curtis, Morris & Safford

[57] ABSTRACT

Process for preparing a derivative of the fragment B of diphtheria toxin, which comprises treating an aqueous solution of the diphtheria toxin with an aliphatic mono- or di-aldehyde having a chain length of 1 to 6 carbon atoms at an aldehyde concentration of 0.0015 M to 0.035 M, at 1° to 20° C, for 5 minutes to 50 hours, reacting the toxin, before or after the treatment with aldehyde, in the presence of a compound splitting off di-sulfide bridges, with a proteolytic enzyme, recovering the derivative of fragment B from the solution obtained in the presence of a denaturing agent by protein-chemical isolation processes and separating it from the denaturing agent.

8 Claims, No Drawings

DERIVATIVES OF DIPHTHERIA TOXIN, PROCESS FOR PREPARING THEM AND AGENTS CONTAINING THEM

The present invention relates to derivatives of diphtheria toxin, to a process for preparing such derivatives by modification of a partial molecule of diphtheria toxin, and to agents, in particular to diphtheria vaccines, which contain one of such derivatives of diphtheria toxin.

Conventional diphtheria vaccines for active immunization contain almost exclusively an antigen prepared by inactivation of diphtheria toxin with formaldehyde. This substance, also called toxoid, is provided with a great number of determinants, of which only few may play a role in the production of protecting antibodies against diphtheria. Elimination of such determinating groups which are of no importance for the protection is desirable in order to obtain antigenic or immunogenic substances which may have higher specificity and may be better tolerated.

Diphtheria toxin is produced by cells of Corynebacterium diphtheriae and set free into the nutrient medium extracellularly as a single polypeptide chain having a molecular weight of about 62,000. Mild proteolysis in the presence of compounds which are capable of splitting disulfide bridges in proteins, for example thiol compounds, produces two characteristic fragments of the diphtheria toxin, i.e. the so-called fragment A (molecular weight about 24,000) coming from the $NH_2$-terminal portion of the toxin and the so-called fragment B (molecular weight about 38,000) coming from the carboxy-terminal portion. Fragment A can be easily isolated by methods of protein chemistry and is stable in native form in physiological buffer solutions. Fragment B, however, can be stored in solution in isolated state only in the presence of denaturing agents such as urea, guanidine hydrochloride or surface-active detergents. Elimination of the denaturing agent then gives a completely water-insoluble fragment B which impedes handling considerably. The not-denatured fragment B, however, is considered to play an important role in the production of protecting antibodies after parenteral administration.

Thus, it was a task of the present invention to modify fragment B of diphtheria toxin in such a manner that it could be kept in solution in a physiologically tolerated medium without loss of its antigenicity. In particular, this fragment B should be able to be used in its modified form as the essential immunogenic constituent of diphtheria vaccines and to replace in these vaccines the conventional formaldehyde toxoid.

Now, we have found that this aim can be achieved by a process the most important feature of which is to avoid the spontaneous irreversible precipitation of fragment B, which can always be observed after elimination of the denaturing agents such as urea, by a slight chemical modification of fragment B either before or after separation of fragment A from the molecular structure of the diphtheria toxin, which is a complex of fragments A and B.

Accordingly, the subject of the present invention is a process for preparing a derivative of fragment B of diphtheria toxin, which comprises treating an aqueous solution of the diphtheria toxin with an aliphatic mono- or di-aldehyde having a chain length of 1 to 6 carbon atoms, preferably formaldehyde, with an aldehyde concentration of 0.0015 M to 0.035 M, preferably 0.002 to 0.02 M, at 1°–20° C, preferably 1°–6° C, for 5 minutes to 50 hours, reacting the toxin, before or after the treatment with aldehyde, in the presence of a compound splitting off disulfide bridges, with a proteolytic enzyme, recovering the derivative of fragment B from the solution obtained in the presence of a denaturing agent by protein-chemical isolation processes and separating it from the denaturing agent.

After isolation of the derivative of fragment B, the denaturing agent is eliminated by dialysis or other comparable methods which permit the separation of low molecular weight substances, for example by gel filtration. The aldehyde used for the reaction and which has not been completely consumed can be eliminated from the batches by similar methods.

The derivative prepared according to the method of the invention, when diluted in physiologically tolerated, isotonically aqueous media, no longer shows the denaturation and precipitation phenomena known from the native fragment B. In the same manner as fragment B, the derivative does not have the toxicity of diphtheria toxin. It has the same behavior as the antigen and is capable of inducing protecting antibodies against diphtheria in the human or animal organism.

The derivative prepared according to the invention can be purified by the conventional protein-chemical methods. However, in view of the high toxicity of the native diphtheria toxin and the fact that protein fractionation methods lead only very seldom to a 100% separation of accompanying substances, especially of those protein bodies having a similar structure, it is of advantage to submit the product prepared according to the invention to another treatment with aldehyde, which treatment comprises combining the derivative of fragment B prepared according to the invention with an aliphatic mono- or di-aldehyde having a chain length of 1 to 6 carbon atoms, preferably formaldehyde, to give an aldehyde concentration of 0.035 to 0.35 M and allowing the whole to stand for 14 to 28 days at 20°–37° C, removing the aldehyde, for example by dialysis, and isolating the modified derivatives of said fragment B.

This additional treatment by aldehyde gives the fragment B an increased stability in aqueous media. Thus, it was assumed that this stable derivative of fragment B could also be obtained by reacting diphtheria toxin, as known in the preparation of fragment B, with a proteolytic enzyme in the presence of substances splitting off di-sulfide bridges, for example thiol compounds, combining the solution with a denaturing agent, recovering the fragment B advantageously by chromatography, in particular by gel filtration, removing the denaturing agent by gel filtration and subsequently allowing the fragment B so obtained, immediately thereafter, to stay together with an aliphatic mono- or dialdehyde having a chain length of 1 to 6 carbon atoms, preferably formaldehyde, at a concentration of 0.0015 ml to 0.035 M, for 5 minutes to 50 hours at 1° to 20° C. If desired, a second treatment with aldehyde for the modification of the derivative may follow. However, the fragment B may also be reacted directly after its isolation with the increased quantity of aldehyde.

Isolation of a modified fragment B from the conventional diphtheria toxoid is not possible, because the use of essentially higher quantities of formaldehyde produces a co-valent cross-linkage between the fragments A and B. However, there is no impeding reason not to react the solution containing the fragment B with aldehydes in order to obtain derivatives having the advantageous properties regarding stability and antigenicity.

As starting materials, there are used diphtheria toxin-containing aqueous media such as those which are also used for the isolation of fragment B, for example culture filtrates which are more or less pre-purified and enriched with regard to diphtheria toxin, highly purified toxin preparations or solutions of fragment B.

Proteolytic enzymes used in the preparation of fragment B are pronase, papain, subtilisin, preferably, however, trypsin, in soluble form or in a form bound to a solid carrier. It has been found advantageous to stop the proteolytic reaction with the aid of an inhibitor, for example trypsin with the aid of a trypsin inhibitor from animal organs or plants. If proteolytic enzymes bound to a carrier are used, the application of inhibitors is not necessary.

As compounds which split off di-sulfide bridges, thiolcompounds are preferred. In this respect, there may be used, for example cysteine, mercapto-ethanol, di-thioerythritol, or preferably di-thiothreitol.

Denaturing agents in the sense of the present invention are chemical compounds with the aid of which a dissociation of hydrogen linkages in protein molecules is made possible. Known agents which dissociate hydrogen linkages are, for example urea or guanidine hydrochloride.

Urea is known for the fact that, with its aid, fragment B can be kept in solution at concentrations of >0.6 M. Advantageously, about 4 to 6 M of urea or about 2 to 4 M of guanidine hydrochloride are used.

In addition to the methods described herein in the present invention, the present invention also relates to derivatives of diphtheria toxin, which derivatives are characterized by the parameters found during their preparation.

Eventually, the invention also relates to agents which contain the diphtheria toxin derivative of the invention, in particular to diphtheria vaccines which are to be used as prophylactic drugs against diphtheria or for the manufacture of diphtheria antisera or also of diagnostic preparations. For increasing the stability in solution of the product of the invention, it may be suitable to add amino-acids or carbohydrates to the physiologically tolerated aqueous medium in which it is dissolved.

The potency of the products as vaccines is proved by the following tests which show the good tolerance and the potency of the products of the invention.

TOLERANCE TEST

Since care must be taken with the conventional formaldehyde toxoid for allergic, delayed reactions, the product of the invention was compared with the conventional toxoid in the following test:

Groups of 10 Guinea pigs each were given:

A. 0.5 ml of the product according to Example 1 with 0.1 mg of protein/ml, adsorbed on 0.02% Al(OH)$_3$-gel and 3 weeks later 0.5 ml of the same antigen with 0.04 mg/ml without Al(OH)$_3$.

B. 0.5 ml of a conventional formaldehyde toxoid with 0.1 mg protein/ml, adsorbed on 0.02% of Al(OH)$_3$ and 3 weeks later 0.5 ml of the same antigen with 0.04 mg/ml without Al(OH)$_3$.

12 Days later, all animals were given intracutaneously 0.1 ml of the two antigens in three dilutions (10 $\mu$g/ml, 1 $\mu$g/ml and 0.1 $\mu$g/ml). The thickness of the skin at the injection site was measured after 24 and 48 hours. The average increase of the thickness of the skin as a measure of the allergic reaction was higher with the conventional toxoid than with the product of the invention.

The average increase of the thickness of the skin is given in 1/10 nm after the injection, as measured with a cutimeter (apparatus for measuring the thickness of the skin manufactured by Messrs. Hauptner)

| | Reaction | |
|---|---|---|
| A. Animals immunized with the product of the invention | 24 hours | 48 hours |
| Challenge with the product of the invention | 5.3 | 0.16 |
| Challenge with conventional toxoid | 7.0 | 1.8 |
| B. Animals immunized with the conventional toxoid | | |
| Challenge with the product of the invention | 5.7 | 3.0 |
| Challenge with conventional toxoid | 9.1 | 4.9 |

POTENCY TEST

Groups of 5 Guinea pigs each were given subcutaneously 0.5 ml (20 $\mu$g) of a suspension of the product prepared according to Example 1, adsorbed on 0.2% Al(OH)$_3$ gel. 4 Weeks later the animals were poisoned with 0.3 mg of diphtheria toxin, corresponding to 10 minimum lethal doses (= dlm = dosis letalis minima). All of the animals survived the poisoning. When the same product was administered in the form of a vaccine free of adsorbate and in a dose of 100 $\mu$g/animal, a survival rate of 20% was obtained.

In order to be able to make a comparison with the condition of humans who already have a diphtheria-antitoxin titer, groups of 5 Guinea pigs each were pre-immunized with the conventional toxoid. The dose of conventional vaccine was so selected that the antitoxin titer after 28 days was always below 0.125 IU/ml of serum. On the 28th day, antigens which had been prepared according to the Examples of the present invention were administered in different doses as adsorbate-free vaccines and the antitoxin titer was determined 10 days later. Animals which had been given 0.2 to 0.4 $\mu$g/animal of the product according to Example 2 showed a 30 to 60-fold increase of the antitoxin titer. The following Examples illustrate the invention:

EXAMPLE 1

Diphtheria toxin (100,000 flocculation units = Lf-units, corresponding to about 270 mg of protein) was combined, as a 0.1% protein solution in a 0.1 M phosphate buffer, at pH 7.8, with formaldehyde up to a final concentration of 0.015 M of aldehyde and allowed to stand for 16 hours at 4° C. The solution was filled into a dialysis hose and dialyzed against the 10-fold quantity of 0.1 M trishydroxymethylaminomethane-HCl buffer (TRIS) having a pH of 8.0, then incubated with trypsin (2 $\mu$g/ml) in the presence of dithiothreitol (DTT) (1.5 mg/ml) for 60 minutes at 37° C and eventually combined with a trypsin inhibitor from bovine lungs (3 $\mu$g/ml). After concentration of the solution to a final concentration of 10 mg of protein per ml on an ultrafilter, urea was added to a concentration of 6 M/l and the solution was introduced into a column (4.5 × 100 cm) of Sephadex$^{(R)}$ G-150 (Trademark of Messrs. Pharmacia, Uppsala), equilibrated with 6 M of urea in 0.1 M of Tris buffer, at pH 8.0, and DTT 0.001 M. Elution was effected with the equilibration mixture. Upon chromatography, three protein peaks were found by measuring the UV absorption at 280 nm. The first, smallest peak represented high molecular weight material which was rejected. The second peak represented the derivative of fragment B. It could be subjected to further purification by repeated chromatography. Peak 3 represented fragment A.

The solution of the isolated derivative of fragment B was diluted with 0.1 M phosphate buffer, at pH 7.8, to 500 ml and then, dialyzed against the same buffer until a qualitative urea analysis became negative. The formaldehyde concentration of the urea-free solution of the derivative of fragment B was then adjusted to 0.07 M and incubated for 21 days at 37° C. After a final dialysis against 0.15 M of NaCl to remove any free formaldehyde, the modified derivative of fragment B was isolated. It was concentrated by ultra-filtration and processed into a vaccine in known manner. As a stabilizer, glycine (0.1 M) or lysine (0.05 M) could be used.

Instead of formaldehyde, there could also be used, referred to the molar quantity of aldehyde, glutardialdehyde, propionaldehyde or butyraldehyde, either in both steps or in one step only, in order to obtain a product with the same properties of easy solubility and good antigenicity.

EXAMPLE 2

Diphtheria toxin (100,000 floculation units = Lf-units, corresponding to about 270 mg of protein) was dialyzed, as 0.1% solution in 0.1 M trishydroxymethylaminomethane-HCl buffer, having a pH of 8.0, then incubated with trypsin (2 µg/ml) in the presence of dithioerythritol (DTE) 1.5 mg/ml) for 60 minutes at 37° C and eventually combined with a trypsin inhibitor of bovine lungs (3 µg/ml). Formaldehyde was then added up to a concentration of 0.015 M of aldehyde and the whole was allowed to stand for 16 hours at 4° C. Urea was added to this solution to a concentration of 6 M/l and the derivative of fragment B was isolated as described in Example 1. If desired, the following reaction with 0.07 M of formaldehyde could be carried out as described in Example 1.

EXAMPLE 3

Diphtheria toxin (100,000 floculation units = Lf-units, corresponding to about 270 mg of protein) was treated, as a 0.1% protein solution, without the pretreatment with 0.015 M of aldehyde, with trypsin in the presence of dithiothreitol as described in Example 1 and then further treated with 0.07 M of aldehyde as described for the reaction of the derivative of fragment B; eventually, the modified derivative of fragment B was isolated.

We claim:

1. A method for preparing a derivative of fragment B of diphtheria toxin, which method comprises treating an aqueous solution of diphtheria toxin with an aliphatic mono-or di-aldehyde having 1 to 6 carbon atoms at an aldehyde concentration from 0.0015 M to 0.035 M, at 1° C to 20° C, for 5 minutes to 50 hours, reacting the toxin, before or after the aldehyde treatment, with a proteolytic enzyme in the presence of a compound splitting disulfide bridges, recovering the so-obtained derivative of fragment B from the solution by protein-chemical isolation processes in the presence of a denaturing agent, and separating said derivative from the denaturing agent.

2. A method for modifying a derivative of fragment B of diphtheria toxin, which comprises combining the derivative of fragment B prepared as claimed in claim 1 with an aliphatic mono- or di-aldehyde having 1 to 6 carbon atoms to give an aldehyde concentration of 0.035 M to 0.35 M, allowing the combination to stand at 20° C to 37° C for 14 days to 28 days, removing the aldehyde, and recovering the resulting modified derivative of fragment B.

3. A modified derivative of fragment B of diphtheria toxin prepared by the method of claim 2.

4. In a diagnostic preparation containing an antigen for diphtheria, the improvement wherein said antigen is a modified derivative of fragment B of diphtheria toxin as claimed in claim 3.

5. In an anti-diphtheria vaccine containing an antigen for diphtheria, the improvement wherein said antigen is a modified derivative of fragment B of diphtheria toxin as claimed in claim 3.

6. A derivative of fragment B of diphtheria toxin prepared by the method of claim 1.

7. In a diagnostic preparation containing an antigen for diphtheria, the improvement wherein said antigen is a derivative of fragment B of diphtheria toxin as claimed in claim 6.

8. In an anti-diphtheria vaccine containing an antigen for diphtheria, the improvement wherein said antigen is a derivative of fragment B of diphtheria toxin as claimed in claim 6.

* * * * *